United States Patent [19]

Decker et al.

[11] 4,095,859
[45] Jun. 20, 1978

[54] PORTABLE EYE EXAMINATION SYSTEM CART

[75] Inventors: Thomas A. Decker; Christian L. Kuether; Robert E. Williams; Dan B. Jones, all of Houston, Tex.

[73] Assignee: Baylor College of Medicine, Houston, Tex.

[21] Appl. No.: 757,107

[22] Filed: Jan. 5, 1977

[51] Int. Cl.² ............................................. A47B 81/00
[52] U.S. Cl. .................................... 312/209; 312/278; 351/38
[58] Field of Search ................... 351/38; 312/209, 250, 312/278

[56] References Cited

U.S. PATENT DOCUMENTS

| 3,041,957 | 7/1962 | Liptay | 312/209 X |
| 3,724,931 | 4/1973 | Nevyas | 351/38 X |

*Primary Examiner*—Paul A. Sacher
*Attorney, Agent, or Firm*—Fulbright & Jaworski

[57] ABSTRACT

A portable eye examination system cart is provided with an instrument console which conveniently supports eye examination devices, an electric power system effective to provide electrical power to the eye examination devices which are electrical, including automatic turn on and off switches when removing and replacing electrical eye examination devices, and a monitor panel. The electrical system may include a rechargeable battery system and recharging circuitry. The cart includes storage areas for convenient location of ophthalmic drugs and examination supplies, small instrument accessories, spare lamps and parts, patient record charts and other miscellaneous items. The cart includes easily manipulated, lockable covers to secure all instruments and supplies from threat of unauthorized use, and the cart is constructed of lightweight material for good maneuverability with dimensions appropriate for convenient use between hospital beds, movement through hospital corridors, and the like.

6 Claims, 6 Drawing Figures

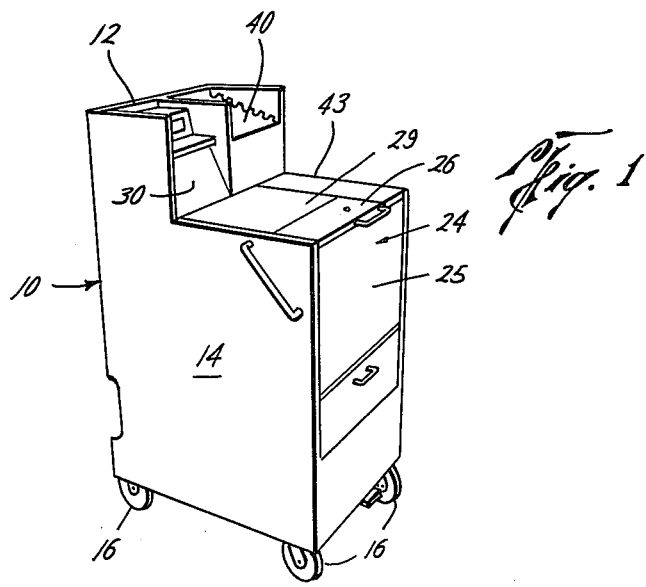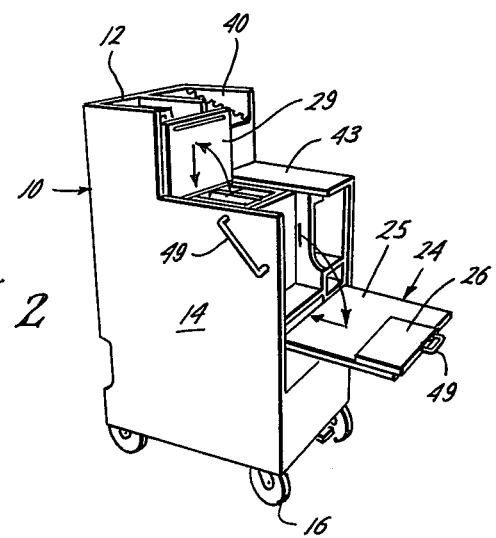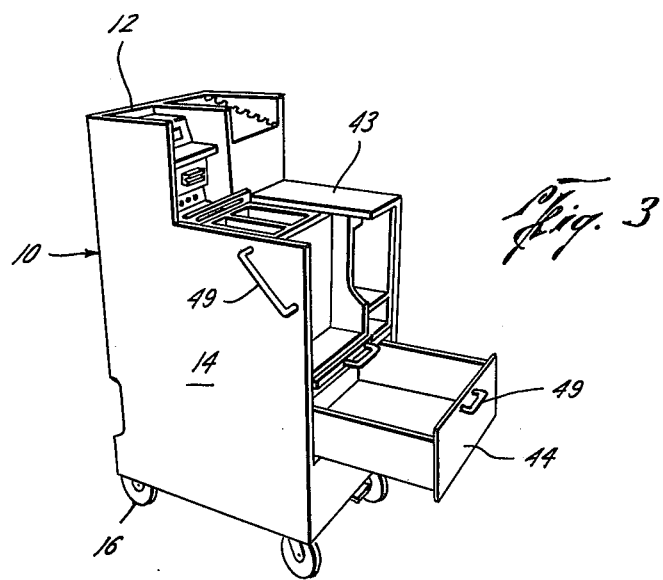

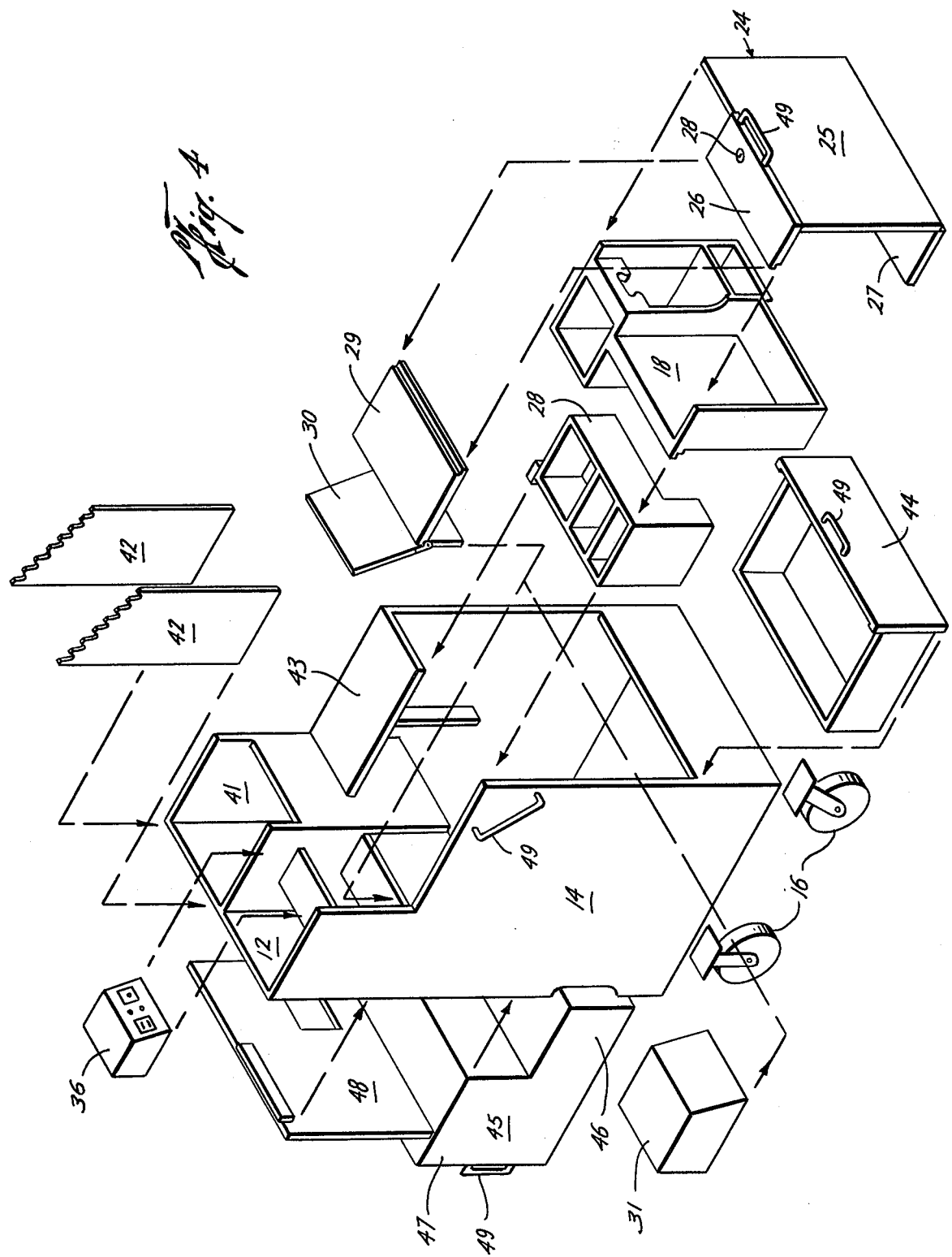

PORTABLE EYE EXAMINATION SYSTEM CART

BACKGROUND OF THE INVENTION

The present invention relates to a portable cart to be used to perform ophthalmic examination on patients who cannot be brought to an ophthalmic clinical facility and to enable medical personnel to perform major portions of an eye examination at a location remote from clinical eye care facilities.

Ophthalmic post-op patients are often confined to their beds or restricted in activity for periods of several days following surgery. The examination of these patients during the physician's hospital rounds is currently limited to tests and observations based on instruments the physician can conveniently carry or place in his pocket, generally a direct ophthalmoscope and a penlight. A small portable cart which stored a number of useful eye examination instruments and, if necessary, provided a power source for their operation could bring much of the capability of the ophthalmic clinic to the patient's bedside and would be useful in other applications such as in an emergency room when time is important or the patient cannot be moved to the ophthalmic clinic. Such a cart would be useful in small, 100 beds or less, hospitals as it would obviate the establishment of much more expensive clinical eye care facilities; and such a cart would be useful in larger hospitals for bedside care as well as emergency room use, it being estimated that currently there are some five thousand emergency rooms in the U.S.A.

While there have been proposed portable carts for a variety of purposes, such as disclosed in the following U.S. Pat. Nos. 3,868,154; 3,428,383; 2,209,294; 3,708,709; 3,715,148; 2,530,233; and 3,520,583; there are no portable eye examination system carts currently available although there has been a need for such carts for a long period of time particularly for the foregoing uses.

SUMMARY OF THE INVENTION

The present invention is directed to a portable eye examination system cart which is ideally suited for emergency room and bedside use and for use in small hospitals and other uses remote from eye clinic facilities. More particularly, the present invention is directed to such a cart which houses eye examination instruments and is provided with an electrical power source including automatic on and off switches for those instruments which are electrically operated, as well as storage areas for convenient location of ophthalmic drugs and examination supplies, small instruments accessories, spare lamps and parts, patient record charts, and other miscellaneous items, and which is small, can easily fit between two hospital beds, is provided with retractable covers to secure and protect instruments and supplies, and preferably which is provided with large wheels for traversing door frames without danger of tipping over.

The portable eye examination system cart includes a body of generally rectangular outline having lockable roller means mounted to its bottom for free rolling movement when unlocked and an instrument console in a front portion of the body and extending to a top portion which supports eye examination instruments and devices. It includes an electric power system effective to provide electric power to the electrically-powered eye examination instruments and devices, including an electric monitoring panel, controls, and the like. The electrical instrument cords attachment to the system's electrical instruments and devices are such to preclude easy unauthorized removal of them from the cart and the mounts of most of them include automatic turn-on of each instrument as it is removed from its respective holder and turn-off when replaced in its holder. The instruments and supplies are located for convenient use, preferably a flat writing surface to conveniently support patient charts or other documents for written entries is provided, the external surfaces are easily cleaned and durable and the cart is constructed of lightweight material for great maneuverability with dimensions appropriate for convenient use between hospital beds, movement through hospital corridors, over door frames, and the like. The eye examination devices and instruments include a portable slit-lamp, direct ophthalmoscope, indirect ophthalmoscope, tonometer, and transilluminator, although other instruments and devices may be housed by the cart as required by the system operator.

Accordingly, it is an object of the present invention to provide a portable eye examination system cart which enables medical personnel to readily perform major portions of an eye examination at locations remote from clinical eye care facilities.

A further object of the present invention is the provision of a small, portable eye examination system cart which stores a number of useful examination instruments and devices, and is provided with a power source for the operation of those which are electrical so that much of the capability of the ophthalmic clinic is brought to the patient's bedside, can be used in emergency rooms when time is important or the patient cannot be moved to the ophthalmic clinic, as well as in other locations remote from eye clinics, and which can serve as an eye clinic.

A further object of the present invention is the provision of a portable eye examination system cart which supports a portable slit-lamp, direct opthalmoscope, indirect ophthalmoscope, tonometer, a transilluminator, and which can house other instruments and devices for eye examination, which has an electric power system including automatic on and off switches for each of the electrical instruments and devices when removed and replaced, and a monitor display of the condition of the cart's electrical system and includes emergency electrical cutoff switches.

A further object of the present invention is the provision of such a portable cart which is easily manipulated, has lockable covers to secure all instruments and supplies from theft or unauthorized use, and in which the electrical instrument cord attachment to the system's electrical examination instruments and devices precludes unauthorized easy removal of the instruments from the cart and convenient mounting of these instruments and devices is provided with automatic turn-on of each instrument as it is removed from its respective holder and turn-off when replaced to prevent unnecessary power drain, such as from an electrical battery power source carried by the cart.

A further object of the present invention is the provision of such a portable eye examination cart in which the instruments and supplies are located for convenient use, which has storage areas for convenient location of ophthalmic drugs and examination supplies, small instrument accessories, spare lamps and parts, patient record charts and other miscellaneous items.

A further object of the present invention is the provision of such a portable eye examination system cart which is constructed of lightweight material for great maneuverability, with dimensions appropriate for convenient use between hospital beds, movement through hospital corridors, over door stoops, down stairs and the like.

Other and further objects, features and advantages of the invention will appear throughout.

BRIEF DESCRIPTION OF THE DRAWINGS

FIG. 1 is a perspective view illustrating a portable eye examination system cart according to the invention.

FIG. 2 is a view of the cart similar to that of FIG. 1 except that the openable covers are illustrated in open position.

FIG. 3 is a perspective view of the cart of FIGS. 1 and 2 showing the open covers in a retracted and out-of-the-way position in the cart for easy access to the eye examination instruments and devices and parts, and the unlocked storage drawers.

FIG. 4 is an exploded perspective view of the eye examination system cart.

FIG. 5 is a front perspective view illustrating the cart with the covers open and retracted for easy access to the ophthalmic instruments and devices, parts, supplies and the like.

DESCRIPTION OF PRESENTLY PREFERRED EMBODIMENTS

Figure 5:
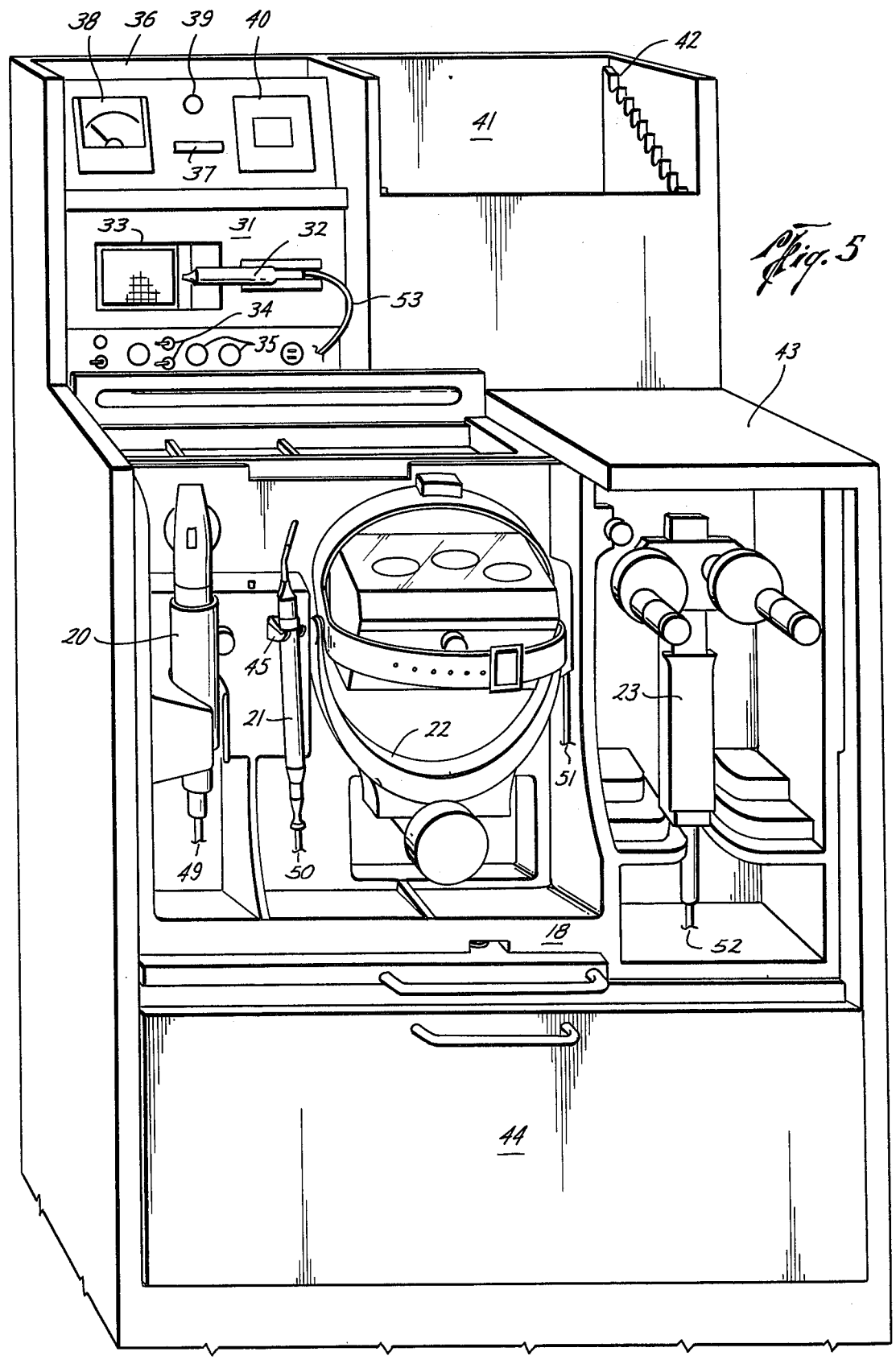

Referring now to the drawings, and particularly to FIGS. 1, 2 and 3 the portable eye examination system cart has a main body or cabinet 10 of generally rectangular outline having a raised upper back panel 12 and vertical side panels 14. Roller means, such as the large wheels 16 are mounted to the bottom of the cabinet 10 for free-flowing movements on floors, over doorstoops, and the like. The cabinet 10 is constructed of lightweight materials for good maneuverability and with dimensions appropriate for convenient use between hospital beds, movement through hospital corridors and the like, and, preferably, the external surfaces are easily cleaned and durable. Such materials include plastic laminate covered plywood, lightweight metals and the like.

Referring now to FIG. 4, an instrument console 18 is mounted in the front portion of the cabinet 10 adjacent its upper portion which is adapted to support eye examination instruments and devices. As best seen in FIG. 5, to which reference is now made, these instruments include a direct ophthalmoscope 20, a transilluminator 21, an indirect ophthalmoscope 22, and a slit-lamp 23.

Referring again to FIG. 4, the instrument console 18 is closed by the openable cover 24 having a vertical panel 25, an upper horizontal panel 26 and a lower horizontal panel 27 which slides under the instrument console 18. The vertical panel 25 is hinged to the horizontally extending upper and lower panels 26 and 27, respectively, which may be locked in place, such as by the lock 28. Thus, the cover 24 completely encloses and covers the instrument console as illustrated in FIG. 1, and can be opened as illustrated in FIG. 2, and moved underneath the console 18 as illustrated in FIG. 3, to be in an out-of-the-way position when using the portable eye examination system cart.

Disposed behind the instrument console 18 is the removable tray 28 which is compartmented as shown for housing and storing ophthalmic drugs and examination supplies. Convenient access is provided by locating the tray 28 directly behind the instrument console 18 which opens in the top and which is covered by the openable cover 29 (as best seen in FIG. 1) hinged to the openable cover 30, both of which can be brought to a vertical position as illustrated in FIG. 2 and slid downwardly into the space behind the tray 28 to provide ready access to the tray 28 and the space adjacent to the back panel 12.

Referring now to FIG. 5, in the embodiment illustrated in the drawings, an electronic tonometer module 31 is disposed directly behind the tray 28 and up against the back of the upright panel 12, which tonometer module 31 is closed by the openable cover 30 when the cart is not in use. The tonometer module 31 includes a tonometer probe 32, recording chart 33 and the usual switches and controls 34 and 35. In the event a manual tonometer is used, the electronic tonometer module 31 can simply be eliminated and the manual tonometer stored in one of the storage areas of the cart. The space previously devoted to the tonometer module 31 can be used to house other instruments or supplies as required or desired.

Disposed on the upright portion 12 immediately above the tonometer module 31 is a monitor panel 36 which includes an emergency shut-off switch 37 and, in the case of a battery power system, a voltage indicator 38 of the battery condition, a battery test switch 39 and a systems status indicator 40, to indicate the condition of the electrical power system, as to whether plugged into the wall outlet, whether engaged in a charging cycle, and the like.

Also disposed on the upright panel 12 is a chart receptacle 41 which includes the hanger brackets 42 for hanging patient charts, although these may be hung on suitable hangers exteriorly of the cart if so desired.

A convenient flat horizontal writing surface 43 is provided on a portion of the top of the cart 10 immediately below the patient chart receptacle 41 and a large storage drawer 44 is provided at the front lower portion of the cabinet for storage of small instrument accessories, spare lamps and parts and other miscellaneous items, and which could readily store a manual tonometer if one were used. Preferably, the storage drawer 44 is locked by the openable cover 24 and is automatically unlatched when the cover 24 is in retracted position. If desired, several smaller drawers or other types of closable storage compartments could be provided instead of one large drawer.

No detailed description is given of any of the electrical eye examination instruments and devices, monitor panel, controls, switches and the like, as these are all readily available on the open market from a variety of manufacturers and suppliers.

Advantageously, on and off switches for the eye examination instruments and devices are provided, such as illustrated at 45 in FIG. 5. Only one such on and off switch is illustrated, but all of the electrical instruments and devices have switches which automatically turn on electrical power to the electrical instruments when the instruments are removed from their supports and which automatically turn off electrical power to the instruments when the instruments are replaced. This eliminates unnecessary use of power and particularly battery drain when having a battery powered electrical system.

In many instances it is desirable to have a battery powered system to provide sufficient electrical power to supply at least 1 day's use of the system's electrical components without battery recharge. As best seen in FIG. 4, an electrical power module 45 is removably provided in the lower portion of the cabinet or body 10 to house the batteries and other electrical components of the electrical system. Preferably, the batteries are housed in the horizontally extending portion 46 and the other electrical components, such as electrical connections, circuit breakers, and the like, are housed in the vertical extending portion 47. The batteries and other electrical components of the power system, as well as switches, controls, indicators and the like are not shown as these are all conventional and are readily available on the market. As illustrated, the power module 45 is in the form of a drawer which slides into the lower rear portion of the cabinet 10 and is provided with the handles 49 for convenience of this purpose. In this connection, various handles, not specifically numbered, are illustrated in the drawings for convenient movement of the cabinet 10 and opening the various openable covers and storage drawer.

The upper portion of the back of the cabinet body 10 is closed by the removable cover 48 which includes additional electrical connections and components, and the cords 49, 50, 51, 52 and 53 of the electrical eye examination instruments and devices 20, 21, 22, 23 and 32, respectively, to the power system through a junction box, not shown, in the upper back portion of the cabinet 10. This insures that the various eye examination instruments and devices cannot readily be removed by unauthorized personnel. The various components, again, in the compartment closed by the cover 48 at the upper portion of the cabinet 10 are all conventional and no detailed description thereof is deemed necessary or given.

Figure 6:
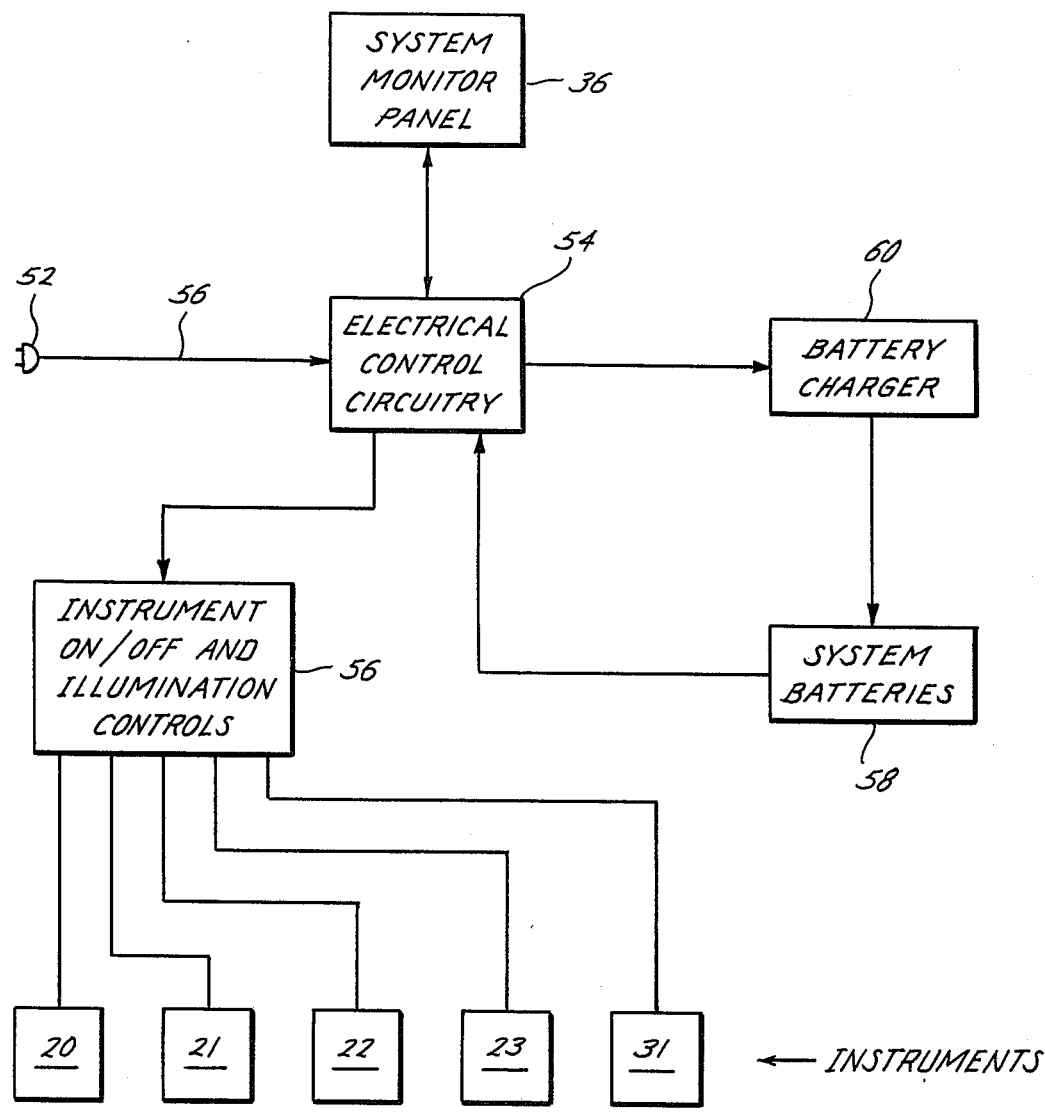
FIG. 6 is a block diagram of the electric circuit of the portable eye examination cart.

Referring now to FIG. 6, a block diagram is illustrated of the electric system. As shown, an electrical plug 52 is connected to the electric control circuitry 54 by the power cord 56. The system monitor panel 36 is suitably electrically connected to the electrical control circuitry 54 by which electrical power is provided through on/off and illumination controls to the instruments such as the direct ophthalmoscope 20, transilluminator 21, indirect ophthalmoscope 22, slit-lamp 23, electronic tonometer module 31, and as many electrical instruments as may be desired.

Preferably, rechargeable batteries 58 and a battery charger 60 are provided so that the electrical system can be operated where there is not a readily accessible electrical power outlet. The system's batteries 58 and battery charger should be sufficient so that electrical power is provided by the batteries for a full day's operation of the various electrical instruments and the batteries can be recharged overnight by simply plugging the plug 52 into a suitable electrical outlet, not shown. As previously mentioned, the control circuitry includes circuit breakers, switches, and other devices necessary to operate the entire system in either the plugged or unplugged condition. The electrical system monitor panel 36 is used as previously described, and the instrument on/off switches and the illuminating controls distribute and control the power provided by the outlet plug with the battery system for each instrument.

No more description is deemed necessary or given as the various electrical components are conventional and are readily available on the open market.

When using the portable eye examination system cart 10, the power module 45 is unplugged from the wall and the plug 52 and power cord stored in the cart by placing it through the opening 51 in the back cover 48. The battery condition is checked by depressing the switch button 39 and reading the meter 38, and the covers 24 and 29, 30, are opened and retracted as previously described to provide ready and convenient access to the various eye examination instruments and devices, and the tray 28 with its supplies. The power switch 34 for the tonometer is turned on and the cart is moved to a particular location for an eye examination of the patient, the patient's charts being disposed in the receptacle 41 and hung on the chart hanger brackets 42. If desired, the portable cart 10 may be moved to the first location for use and then the covers opened and retracted. Then the eye examination of the patient can proceed, removal of the eye examination instruments 20, 21, 22 and 23 from their holders automatically turning on electrical power to each of them, and electrical power being turned off upon replacement of them in their respective holders. The flat surface 43 provides a convenient place for making entries on the patient chart, not shown, which is removed from the chart hangers 42 for this purpose and then replaced.

Any number of eye examinations of patients can be conducted, simply by moving the cart from location to location.

When it is desired to store the cart, electrical power to the tonometer is turned off by the switch 34, all instruments should be checked to see that they are properly stored and in their hangers so that electrical power to them is turned off, all instrument cords are properly stored and located in their respective compartments, the lockable covers are then pulled out and placed in the positions illustrated in FIG. 1 and locked in place. In this connection, locking the cover 24 effectively locks the drawer 44 in position. The plug 52 is then plugged into an electrical outlet for recharging of the batteries. As previously mentioned, manual eye examination instruments, such as a manual tonometer, can be used, and, if desired, the battery system can be eliminated with a simple plug-in cord for plugging into electrical outlets at locations of the patients.

The present invention thus provides a portable eye clinic by which eye examinations of patients can be done quickly and readily at locations remote from the usual eye clinic.

The present invention, therefore, has the advantages and features and obtains the objects and ends mentioned as well as others inherent therein.

While presently preferred embodiments have been given for the purpose of disclosure, various changes and additions can be made therein which are within the spirit of the invention as defined by the scope of the appended claims.

What is claimed is:

1. A portable eye examination system cart comprising,
   a body of generally rectangular outline,
   roller means mounted to the bottom of the body for free rolling movement,
   an instrument console in the front portion and extending to a top portion of the body, the console including means to support eye examination instruments and devices,
   an openable cover enclosing the front and the top portion of the body, an electric power system carried by the cart effective to provide electric power to the eye examination instruments and devices which are electrically operated, the electric power system including an indicator mounted on the cart indicating whether the electric power system is on and off, an emergency on and off switch, and a plug for an electric outlet, the means to support the eye examination devices including on and off switches for one or more of the eye examination instruments and devices which are electrically operated arranged to be in an off position when supporting and in an on position when not supporting them, the body including a closable storage compartment and means for carrying patient charts, and a tray disposed at the upper portion of the body for containing supplies.

2. The portable eye examination system cart of claim 1, where, the body has a raised upper back portion with the indicator and emergency on and off switch located thereon, and including a second openable cover enclosing at least part of the back portion and part of the top portion over the tray.

3. The portable eye examination system cart of claim 2, where the means for carrying patient charts comprises a compartment located in the upper back portion opening into the cart's top.

4. The portable eye examination system cart of claim 2, where, the means to support eye examination instruments and devices includes means for supporting a portable slit-lamp, a direct ophthalmoscope, and indirect ophthalmoscope and a transilluminator, and the cart has means for supporting an electrical tonometer and chart at the raised upper back portion of the cart which is closed by the second openable cover, and the last-mentioned means including an on and off electrical power switch and an indicator for the status of the electrical supply to the tonometer.

5. The portable eye examination system cart of claim 1, where the electric power system includes rechargeable battery power and recharging means carried by the cart.

6. The portable eye examination system cart of claim 4, where the electric power system includes rechargeable battery power and recharging means carried by the cart.

* * * * *